United States Patent
Lecolier et al.

(10) Patent No.: US 10,495,577 B2
(45) Date of Patent: Dec. 3, 2019

(54) SYSTEM FOR MEASURING THE QUANTITY OF SEMICONDUCTOR NANOCRYSTALS PRESENT IN A FLUID

(71) Applicant: IFP Energies nouvelles, Rueil-Malmaison (FR)

(72) Inventors: Eric Lecolier, Chaville (FR); Patrick Gateau, Maurepas (FR)

(73) Assignee: IFP ENERGIES NOUVELLES, Rueil-Malmaison (FR)

( * ) Notice: Subject to any disclaimer, the term of this patent is extended or adjusted under 35 U.S.C. 154(b) by 0 days.

(21) Appl. No.: 15/575,739

(22) PCT Filed: May 11, 2016

(86) PCT No.: PCT/EP2016/060536
§ 371 (c)(1),
(2) Date: Nov. 20, 2017

(87) PCT Pub. No.: WO2016/184744
PCT Pub. Date: Nov. 24, 2016

(65) Prior Publication Data
US 2018/0292322 A1    Oct. 11, 2018

(30) Foreign Application Priority Data
May 21, 2015   (FR) ...................... 15 54562

(51) Int. Cl.
*G01N 21/64*    (2006.01)
*G01N 21/85*    (2006.01)

(52) U.S. Cl.
CPC ....... *G01N 21/6489* (2013.01); *G01N 21/645* (2013.01); *G01N 21/6428* (2013.01); *G01N 21/85* (2013.01)

(58) Field of Classification Search
CPC .. G01N 21/6248; G01N 21/645; G01N 21/85; G01N 21/6489
See application file for complete search history.

(56) References Cited

U.S. PATENT DOCUMENTS

| | | | |
|---|---|---|---|
| 2001/0049101 A1* | 12/2001 | Brogger | B82Y 10/00 435/6.11 |
| 2004/0197929 A1 | 10/2004 | Lagwinski et al. | |
| 2005/0048581 A1* | 3/2005 | Chiu | B01L 3/502761 435/7.1 |

(Continued)

FOREIGN PATENT DOCUMENTS

| | | |
|---|---|---|
| EP | 2853884 A1 | 4/2015 |
| WO | 2004/023118 A1 | 3/2004 |

(Continued)

OTHER PUBLICATIONS

International Search Report for PCT/EP2016/060536, dated Aug. 5, 2016; English translation submitted herewith (7 pgs.).

*Primary Examiner* — David E Smith
(74) *Attorney, Agent, or Firm* — Fitch, Even, Tabin & Flannery, LLP (57) ABSTRACT

The present invention concerns a system for measuring the quantity of fluorescent semiconductor nanocrystals present in a fluid. The system in accordance with the invention comprises a fluid circulation device (1), a light source (2) and a fluorescence detector (3) for the semiconductor nanocrystals (4).

16 Claims, 4 Drawing Sheets

(56) References Cited

U.S. PATENT DOCUMENTS

| | | | |
|---|---|---|---|
| 2006/0014175 A1* | 1/2006 | Naasani | B82Y 15/00 |
| | | | 435/6.12 |
| 2007/0185679 A1* | 8/2007 | Petruno | G01N 21/6428 |
| | | | 702/117 |
| 2010/0133200 A1* | 6/2010 | Gin | G01N 21/05 |
| | | | 210/742 |
| 2010/0243570 A1* | 9/2010 | Mayer | C02F 1/36 |
| | | | 210/665 |
| 2012/0043477 A1* | 2/2012 | Hegazi | G01N 21/274 |
| | | | 250/459.1 |
| 2013/0043194 A1 | 2/2013 | McNeel et al. | |
| 2013/0340518 A1* | 12/2013 | Jones | E21B 49/005 |
| | | | 73/152.55 |
| 2014/0249053 A1 | 9/2014 | Robinson et al. | |
| 2014/0260694 A1* | 9/2014 | Szlendak | E21B 47/1015 |
| | | | 73/863.51 |
| 2016/0009580 A1* | 1/2016 | Elbicki | C02F 1/281 |
| | | | 210/605 |
| 2016/0363693 A1* | 12/2016 | Murugesan | G01N 21/643 |

FOREIGN PATENT DOCUMENTS

| | | | | |
|---|---|---|---|---|
| WO | 2013/062640 A1 | | 5/2013 | |
| WO | WO 2013062640 A1 * | | 5/2013 | G01N 21/65 |
| WO | WO-2013062640 A1 * | | 5/2013 | G01N 21/65 |

* cited by examiner

SYSTEM FOR MEASURING THE QUANTITY OF SEMICONDUCTOR NANOCRYSTALS PRESENT IN A FLUID

CROSS-REFERENCE TO RELATED APPLICATIONS

This application is a U.S. national phase application filed under 35 U.S.C. § 371 of International Application No. PCT/EP2016/060536, filed May 11, 2016, designating the United States, which claims priority from French Patent Application No. 15/54.562, filed May 21, 2015, which are hereby incorporated herein by reference in their entirety.

The present invention relates to the field of systems for detecting and measuring the quantity of semiconductor nanocrystals present in a fluid, in particular in the field of treatment of water, and monitoring aquifers located above a reservoir of source rock oils and gas.

In the various water treatment processes, for example for the treatment of the water produced during exploration or development operations in hydrocarbon reservoirs or for the treatment of water which has to be depolluted, it is important to be aware of the presence, nature and concentration of the molecules present in the water, these molecules constituting pollution for the water. Thanks to this information, it is then possible to select and adapt the water treatment process as a function of its degree of pollution.

In order to characterize the composition of a liquid, it may be envisaged to use labels for the molecules to be identified and determined, these labels being luminescent semiconductor nanocrystals (fluorescent or phosphorescent), for example. A luminescent semiconductor nanocrystal is also known as a quantum dot. A luminescent semiconductor nanocrystal is a nanostructured semiconductor. Depending on its size and its characteristics, it behaves as a potential well which confines electrons (and holes) in three-dimensions in space in a region with a size of the order of the wavelength of the electrons (de Broglie wavelength), i.e. a few tens of nanometres in a semiconductor. Semiconductor nanocrystals (or nanoparticles) are objects with a size which is typically in the range 2 to 20 nm; these nanoparticles comprise approximately 100 to 10000 atoms. Because of their small size, the semiconductor nanocrystals have very specific optical properties (for example photoluminescence) due to the atypical behaviour of the electrons because of their confinement in these semiconductor nanocrystals. Thus, quantum dots are known and renowned for their fluorescence and phosphorescence when they are excited by electromagnetic radiation. Fluorescent semiconductor nanocrystals have the particularity of fluorescing at very narrow wavelengths (the width at mid-height of the emission peak is typically 30 nm). The quantum dots may emit in the ultraviolet, the visible, the near infrared and the infrared. In addition, their absorption spectrum is very broad: thus, they can be excited with radiation of different wavelengths.

However, there is currently no equipment that can be used for in-line determination of the quantity of luminescent semiconductor nanocrystals present in a fluid, nor any equipment which can be used for in-line measurement of the quantity of fluorescent semiconductor nanocrystals present in a fluid. In addition, in the field of the treatment of water obtained from oil production, there is currently no equipment which is easy to use which can be used to detect the presence, or for in-line measurement the quantity, of additives present in a fluid produced at the surface. The term "additive" designates surfactants, monomers, polymers, copolymers, minerals (clays, barite, etc), oxide particles (titanium oxides, iron oxides, etc). In fact, existing analysis techniques cannot be used to distinguish the hydrocarbon molecules present in the production water from the additives (organic molecules, polymers, surfactants) also present in this water. Traditional analysis techniques are based on measuring the total organic carbon (TOC) or the UV spectrum. The measurement of the total organic carbon indicates the quantity of organic compounds in the fluid which is analysed. However, analysis of the TOC cannot be used to differentiate the molecules of additives from the molecules of hydrocarbons since they all comprise the element carbon. The UV-visible absorption spectrophotometry is based on absorption by the sample of electromagnetic radiation in the ultraviolet or visible range. This technique based on material-radiation interactions involves electronic transitions in the atoms composing the molecules. UV-visible absorption spectrophotometry is an analytical method which can be used to quantitatively assay the compounds in solution, using the Beer-Lambert equation:

$$\frac{I}{I_0} = \varepsilon_\lambda \cdot \ell \cdot C$$

where $I_0$ is the incident intensity, I is the intensity of the radiation measured after passing over the distance l in the sample to be analysed, $\varepsilon_\lambda$ is the molar absorption coefficient (which depends on each molecule and the wavelength), and C is the molar concentration of the fluid.

It is well known, for example, that molecules comprising a benzene ring may be determined by UV-visible absorption spectrophotometry. In fact, a benzene ring excited by an electromagnetic radiation absorbs at three different wavelengths (271, 263 and 254 nm). Thus, using Beer-Lambert's law, it is possible to determine such molecules either from a calibration curve, or by means of knowledge of the molar extinction coefficient. Thus, benzene rings grafted to the additives to be determined could be envisaged. However, there are aromatic hydrocarbons in the crude oils produced which are compounds with a molecular structure which comprises at least one benzene ring. The consequence is that these aromatic hydrocarbons will also be detected by UV-visible absorption spectrophotometry and will thus interfere with the signal for the desired additives. Thus, the analysis method is non-discriminating and cannot be used to detect and determine the additives of interest. Thus, the present invention concerns a system for the detection and/or measurement of the quantity of luminescent semiconductor nanocrystals present in a fluid. The system in accordance with the invention comprises a fluid circulation device, a light source, and a detector for the fluorescence and/or phosphorescence of the luminescent semiconductor nanocrystals. Thus, the present invention can be used to detect and/or measure the quantity of luminescent semiconductor nanocrystals present in a fluid continuously and in-line. The measuring system in accordance with the invention can also be used to identify the presence of additives in a fluid and to measure their quantities, when these additives are labelled with semiconductor nanocrystals. Furthermore, the measuring system in accordance with the invention can be used to monitor an aquifer during development of source rock oils and gas.

THE SYSTEM IN ACCORDANCE WITH THE INVENTION

The invention concerns a system for the detection and/or measurement of the quantity of at least one luminescent semiconductor nanocrystal present in a fluid. Said system for detection and/or measurement comprises a device for circulating said fluid, a light source orientated towards said device for circulating said fluid, and a detector which is capable of detecting and measuring the luminescence from said semiconductor nanocrystal, said detector being orientated towards a zone of said fluid circulation device exposed to light radiation from said light source.

In accordance with the invention, said fluid is a complex solution or an aqueous liquid.

In accordance with one embodiment of the invention, said semiconductor nanocrystal labels a molecule which is potentially present in said fluid.

In accordance with a variation, said device for circulating said fluid is a channel bypassing a conduit in which said fluid circulates.

In accordance with a variation, said device for circulating said fluid is a microfluidic chip.

Advantageously, said measuring system comprises at least one valve on each side of said circulation device.

In accordance with one feature of the invention, said light source emits monochromatic radiation.

Alternatively, said light source emits polychromatic radiation.

Advantageously, said light source emits polarized radiation.

In accordance with one embodiment of the invention, said detector is placed substantially at 90° or at 180° with respect to the incident beam emitted by the light source around said fluid circulation device.

In accordance with one design of the invention, said detector is placed downstream of the source, with respect to the direction of circulation of fluid, at a longitudinal distance from the light source.

Preferably, said detector comprises a photomultiplier and means for measuring the fluorescence and/or phosphorescence emission spectrum.

In accordance with one embodiment, said detector comprises a device for measuring the intensity of the diffused light.

Furthermore, the invention concerns a facility for the treatment of an aqueous liquid, comprising means for treatment of said liquid, means for selective distribution of said liquid comprising at least two outlets, a transport conduit connecting said treatment means and said selective distribution means, and a system for detection and/or measurement in accordance with one of the preceding features. Said selective distribution means are programmed to distribute the liquid towards one of said outlets as a function of the measurement from said measuring system.

In accordance with one variation, said detection and/or measuring system is disposed in a channel bypassing said transport conduit.

Alternatively, said detection and/or measuring system are disposed in said transport conduit.

In addition, the invention concerns a use of a system for the detection and/or measurement in accordance with one of the preceding features in order to determine the quantity of additive present in the water produced by a process for exploration or development of a subterranean formation, said additive being labelled with said semiconductor nanocrystal.

The invention also concerns a use of a system for the detection and/or measurement in accordance with one of the preceding features in order to determine pollution in water for a purification station and/or a water depollution station of an industrial facility.

Furthermore, the invention concerns a use of a system for detection and/or measurement in accordance with one of the preceding features, in order to monitor an aquifer during a process for the development of source rock oils and/or gas.

Furthermore, the invention concerns a method for the detection and/or measurement of the quantity of at least one luminescent semiconductor nanocrystal present in a fluid. In this method, the following steps are carried out:

a) the fluid is circulated in a circulation device;

b) said circulation device is irradiated with light radiation; and c) the luminescence of said semiconductor nanocrystal is detected and/or measured in a zone of said fluid circulation device, said zone being exposed to said light radiation.

BRIEF DESCRIPTION OF THE FIGURES

Further characteristics and advantages of the method in accordance with the invention will become apparent from the following description below of non-limiting examples of embodiments, made with reference to the accompanying figures which are described below.

DETAILED DESCRIPTION OF THE INVENTION

The system in accordance with the invention can be used to detect the presence of luminescent semiconductor nanocrystals (fluorescent, phosphorescent) present in a fluid and/or to determine the quantity of luminescent semiconductor nanocrystal (fluorescent, phosphorescent) present in a fluid.

The system in accordance with the invention can also be used to detect the presence and/or to determine the quantity of an additive present in a complex fluid (aqueous solutions of organic solutes, dispersions of nanoparticles, oil-in-water emulsions, water-in-oil emulsions, micro-emulsions, oils, etc), this additive having been labelled deliberately with at least one fluorescent semiconductor nanocrystal. In the case of a quantitative measurement, labelling the additive with at least one fluorescent semiconductor nanocrystal is carried out in a manner such that the number of fluorescent semiconductor nanoparticles per additive entity is known (for example, in the case of polymers, the number of fluorescent semiconductor nanocrystals per polymer chain is known). The fluid is preferably an aqueous liquid. In the remainder of the description, the measuring system is described principally for use with water (aqueous liquid). However, the measuring system in accordance with the invention is adapted to any type of complex fluid such as crude oils, mineral oils, vegetable oils, water-in-oil emulsions, oil-in-water emulsions, micro-emulsions, aqueous dispersions of nanoparticles (such as suspensions of clays, calcium silicates, etc), organic dispersions of nanoparticles, industrial effluents, etc.

The measuring system in accordance with the invention comprises:

- a fluid circulation device, i.e. a device in which the fluid flows. Thus, the measurement may be carried out on a liquid in motion, which means that a continuous in-line measurement can be carried out. The fluid circulation device may be substantially in the shape of a channel (with a circular or non-circular section) or a micro-channel (with a circular section, with a parallelepipedal section, or with a section with a specific shape adapted to the envisaged application). The fluid which circulates in the circulation device (duct, pipe, channel, micro-channel, etc) may be under high pressure (for example, several hundred bars). The fluid may flow in the measuring system under the effect of the flow of fluid prevailing in the principal conduits in which the fluid to be analysed is flowing, or under the effect of the natural flow prevailing in the aquifers, ground water. For the majority of applications, one advantage of the measuring system is that it does not need a pump to cause the fluid to circulate in this measuring system, it being understood that this is already moving.
- a light source; the light source is orientated towards the fluid circulation device. As an example, the light source may be a laser, a photodiode, a lamp, etc. The light source may be a monochromatic or polychromatic source. In addition, the light source may emit polarized or non-polarized radiation; this polarization may be a supplemental advantage in detecting and identifying the luminescent semiconductor nanocrystals more easily, and finally be in a position to identify various natures of the additives.
- a detector for detecting the radiation emitted by the fluorescence and/or the phosphorescence from the semiconductor nanocrystal. The detector is orientated towards a zone of the fluid circulation device which is exposed to light radiation from the light source used. In order to optimize the detection of the radiation emitted by the luminescent semiconductor nanocrystal, the detector may be placed at substantially 90° or 180° to the light source with respect to the fluid circulation means. In the case in which the detector can be used to measure phosphorescence, the measuring system can be used to demonstrate the presence of phosphorescent nanoparticles in the fluid, or of additives labelled with the phosphorescent nanoparticles. In the case in which the detector can be used to measure the intensity of fluorescence, which is substantially proportional to the quantity of fluorescent semiconductor nanocrystals, the measuring system can be used to determine the quantity of fluorescent semiconductor nanocrystals. In the case in which these fluorescent semiconductor nanocrystals are grafted onto additives, the measuring system can finally determine the concentration of additives to be identified and determined. In the case in which it is simply desired to detect the presence of luminescent semiconductor nanocrystals or additives labelled with luminescent semiconductor nanocrystals, the detector may be an optical apparatus (optical microscope, binocular microscope, camera, rapid or ultra-rapid camera, miniature camera, CCD camera, photographic apparatus) which can be used to observe the points of light which are characteristic of the presence of luminescent semiconductor nanocrystals. The resolution and sensitivity of the optical apparatus are adapted to the application and to the measuring system in order to be able to observe the points of light.

In accordance with one embodiment of the invention, the radiation emitted by the light source and the detector are adapted to the wavelength of the fluorescent radiation emitted by the luminescent semiconductor nanocrystals to be detected. The light source may have any wavelength, because the luminescent semiconductor nanocrystals can be excited over a broad range of the electromagnetic spectrum. Depending on the application, one or more wavelengths may advantageously be selected which can optimize the measurement of the intensity of luminescence emitted by the semiconductor nanocrystals. These wavelengths may be in the ultraviolet, the visible or the infrared, depending on the characteristics (sizes, shapes, chemical compositions, surface properties, etc) of the luminescent semiconductor nanocrystals used. The advantage of the luminescent semiconductor nanocrystals resides in the fact that their emission spectra cannot be confused with those emitted by other molecules present in the fluids to be analysed (hydrocarbon molecules, for example). Thus, there is no possibility of interference from other compounds contained in the complex fluid being analysed. In a particular embodiment of the invention, polarizers may be used; these polarizers may be installed between the light source and the zone of the circulation device which is illuminated, between the illuminated zone of the circulation device (corresponding to the portion of the fluid being analysed) and the detection means. These polarizers can be used to polarize the light emitted at a wavelength optimizing the fluorescence of the semiconductor nanocrystals, which facilitates their detection.

Advantageously (and for all of the embodiments of the invention), when the analysis is carried out when the fluid flows, the detector may be installed in a manner such that it does not face the light source, but it could be offset longitudinally (in the direction of circulation of fluid) because the semiconductor nanocrystals emit light over several milliseconds or even several seconds following excitation: in this configuration, the incident radiation does not perturb the measurement of the intensity of fluorescence or phosphorescence. Irrespective of this, one of the advantages of using luminescent semiconductor nanocrystals resides in the large separation between the excitation and emission wavelengths, which is highly advantageous as regards detection because the risk of interference can be avoided by carefully selecting the excitation wavelength and the emission wavelength by selecting, for the latter, good properties for the luminescent semiconductor nanocrystals (nature of the atomic elements, size of the nanocrystals, doping impurities for the semiconductor, for example). As an example, the light source and the system for measuring the intensity of fluorescence or phosphorescence may be separated at most by a distance d (in the direction of flow of fluid) such that d is equal to the rate of flow of fluid, v, multiplied by the maximum duration of the fluorescence or phosphorescence, t, of the luminescent semiconductor nanocrystals, assuming that the luminescent semiconductor nanocrystals and/or the additives labelled with the luminescent semiconductor nanocrystals are displaced at the same velocity as the fluid.

In accordance with one embodiment of the invention, in order to be able to determine the quantity of semiconductor nanocrystals with more accuracy, the signal-to-noise ratio should be improved. The noise might be electronic noise (which is independent of the light intensity); in this case, the electronic noise may be corrected using electronic signal processing devices which are known to the person skilled in the art. The noise might be due to an unwanted optical signal such as light diffusion; however, this noise is proportional to the light intensity. When the measuring system is used to determine luminescent semiconductor nanocrystals in a diffusing complex fluid, the measuring system may additionally comprise a device for measuring the intensity of the diffused light: this measurement can then significantly improve the signal to noise ratio of the light. The device for measuring the diffused intensity may employ diode lasers emitting at different wavelengths (at least one of which is beyond the absorption spectrum of the semiconductor nanocrystals), coupled with optical fibres and to a photo-multiplier (or another photon counting device). The light beam with the wavelength beyond the absorption spectrum of the luminescent semiconductor nanocrystals acts as a reference for measuring the intensity of the diffused light.

Advantageously, the liquid circulation device may have the form of a channel, which may be substantially tubular. The channel may be produced from a completely transparent material, so as to be able to allow light radiation to pass from the light source towards the detector. Alternatively, the channel may be transparent solely at the position of the light source and detector. When the detector is installed in a facility functioning under pressure or under high pressure conditions (for example an aquifer where the pressure may be several hundred bars), the light source and the detector may be installed either at a viewport or with the aid of a pressure-resistant and sealed connector, or using a pressure-resistant and sealed flange, or with the aid of any means or assembly of means (ring, ferrule, washer, O ring, etc) for making a pressure-sealed connection which is known to the person skilled in the art.

In accordance with one embodiment of the invention, the fluid circulation device is in the form of a bypass (for example a bypass channel) of a conduit in which the fluid to be analysed is circulating. The term "bypass" is used for a circuit which goes round a portion of the conduit. The bypass channel corresponds substantially to an assembly in parallel to the measuring system with respect to the conduit. Thus, in-line measurement is facilitated and the circulation of fluid is not perturbed by the measurement. In order to carry out the measurement periodically, for example at regular intervals, the fluid circulation device may comprise at least one valve to prevent the fluid from circulating in the principal conduit and pass it through the measuring system.

In another embodiment of the invention, the bypass channel may be filled with the fluid to be analysed in a manner such as to carry out the analysis without any flow. In this case, another valve is installed in the outlet from the bypass. In order to isolate the fluid to be analysed in the bypass, the valves installed at the inlet and at the outlet of the bypass are closed. The presence of these valves means that the fluid to be analysed can be isolated in the measuring system. These valves may be actuated manually or may be operated automatically (for example using a solenoid valve).

In accordance with another embodiment of the invention, the measuring system may be installed directly inside the principal conduit in which the fluid to be analysed is moving (it is not necessary to install the measuring system in a bypass of the principal conduit). In accordance with one embodiment, the measuring system may be in the form of a hollow tube, this tube being maintained and centred in the principal conduit by rods or bars resting on the internal walls of the principal conduit. At each end of the measurement chamber, shutters may be provided so as to fill the chamber and carry out the measurement on a fluid which is not flowing.

In accordance with a variation of the invention (which may be combined with any one of the variations described above), the fluid circulation device is a microfluidic chip. The microfluidic chip can operate under pressure. The manufacture of microfluidic chips functioning with pressurized fluids has been described in the scientific literature (Lorber and al., Some recent advances in the design and the use of miniaturized droplet-based continuous process: Applications in chemistry and high-pressure microflows, Lab on a Chip, 2011, 11, 779; Pinho and al., A microfluidic approach for investigating multicomponent system thermodynamics at high pressures and temperatures, Lab on a Chip, 2014, 14, 3843). A microfluidic chip is an assembly of micro-channels engraved or moulded into a material (glass, silicon or polymer such as PDMS, standing for PolyDiMethylSiloxane). The micro-channels constituting the microfluidic chip are connected together in a manner such as to carry out a desired function (mixing, pumping, sorting, monitoring a biochemical environment, measurements, chemical analyses). This network of micro-channels enclosed in the microfluidic chip is connected to the outside via at least one inlet and at least one outlet pierced through the chip, such as interfaces between the macroscopic and microscopic world. The liquids (or gases) are injected into and evacuated from the microfluidic chip via these holes (through the tubes, syringe adapters or even simple holes in the chip) to and from the active exterior systems (pressure controller, syringe pump or peristaltic pumps) or passive means (for example hydrostatic pressures).

In this variation, the light source and the detector are adapted to the micro-channels and are also of reduced size, which means that the bulk of the measuring system can be reduced. As an example, the light source may be a laser diode or any other device which can be used to illuminate the micro-channels over their entire length. The light source is fixed directly to the microfluidic chip. In the case in which the width of the micro-channel in which the fluid is circulating is greater than the diameter of the zone illuminated by the light source, the optical elements necessary to enlarge the beam are integrated into the measuring system so as to illuminate the entirety of the micro-channel. The fluorescence and/or phosphorescence signal can be detected by means of a photodetector (for example a photodiode) which is fixed directly to the microfluidic chip downstream of the light source with respect to the direction of flow of fluid in the channels.

Suitable electronic amplification means may be used to analyse the luminescence signal. The emitted luminescence signal may be focussed onto a zone where a reduced sized spectrophotometer is placed or, in another option, the signal emitted may be focused onto a zone where an optical fibre is connected to a spectrophotometer or any other apparatus which can be used to measure a flow of photons. In the case in which the presence of luminescent semiconductor nanocrystals or additives labelled with the luminescent semiconductor nanocrystals are simply to be detected and not determined, the detector may be an optical apparatus (optical microscope, binocular microscope, camera, rapid camera or ultra-rapid camera, miniature camera, CCD camera, photographic apparatus) in order to observe the points of light characteristic of the presence of the luminescent semiconductor nanocrystals. The resolution and sensitivity of the optical apparatus are adapted to the application and to the dimensions of the microfluidic chip in order to be able to observe the points of light.

In accordance with one feature of the invention (which may be combined with the various embodiments), the detector comprises at least one photomultiplier and means for measuring the fluorescence and/or phosphorescence emission spectrum. The photomultiplier can be used to collect and optionally amplify the emission signal from the fluorescent and/or phosphorescent radiation. The means for measuring the fluorescence emission spectrum are precise and discriminating given the very specific optical properties of fluorescent semiconductor nanocrystals. By means of this detector, the concentration of fluorescent semiconductor nanocrystals is directly proportional to the intensity of the measured fluorescence. Thus, it is possible to directly and rapidly determine the quantity of semiconductor nanocrystals present in the fluid, or the concentration of additives in the fluid.

In accordance with one design of the measuring system, when the light source is a polychromatic source, the detector is placed at substantially 90° with respect to the incident radiation from the light source. Thus, detection is more precise. However, given that the excitation and emission wavelengths of the luminescence may be substantially separated as a function of the properties of the semiconductor nanoparticles, the measuring system may function irrespective of the angle between the incident radiation and the detector, especially when a phosphorescence signal is to be measured.

The measuring system in accordance with the invention may be installed in surface facilities (in particular to monitor the operations for the treatment of production water from the oil industry, and thus to monitor the quality of the treated water) or may be installed in subterranean formations (for example in aquifers, aquitards, or ground water) in order to detect any pollution induced by the additives used in geoengineering operations such as drilling, or hydraulic fracturing, in which at least one of the additives to the fluids used has been labelled with at least one semiconductor nanocrystal. For these operations, a plurality of measuring systems may be installed. These measuring systems may be installed permanently or semi-permanently in wells drilled especially to bury these pollution detectors in the subterranean formations to be monitored. These measuring systems may either allow the presence of luminescent nanoparticles to be detected in a geological stratum where they are not supposed to be found (so as to provide evidence of a leak), or can be used to measure the concentration of fluorescent nanoparticles in formation water or to measure the concentration of additives labelled with at least one fluorescent semiconductor nanocrystal. A system for measuring the concentration of fluorescent nanoparticles or additives labelled with fluorescent nanoparticles can be used to monitor, over time, the change in the leak (increase, decrease) and thus to assess the pertinence of remedial solutions implemented to stop the leak.

It will be recalled that a semiconductor nanocrystal is also known as a quantum dot. A semiconductor nanocrystal is a semiconducting nanostructure. Depending on its size and its characteristics, it behaves as a potential well which confines the electrons (and holes) in three-dimensions in space in a region with a size of the order of the wavelength of the electrons (de Broglie wavelength), i.e. a few tens of nanometres in a semiconductor. Semiconductor nanocrystals (or nanoparticles) are objects with a size which is typically in the range 2 to 20 nm; these nanoparticles comprise approximately 100 to 10000 atoms. Because of their very small size, the semiconductor nanocrystals have very specific optical properties due to the atypical behaviour of the electrons because of their confinement in these semiconductor nanocrystals. Thus, quantum dots are known and renowned for their luminescence. Certain semiconductor nanocrystals can fluoresce at very narrow wavelengths (the width at mid-height of the emission peak is typically 30 nm) and other semiconductor nanocrystals are phosphorescent. The quantum dots may emit in the ultraviolet, the visible, the near infrared and the infrared. In addition, their absorption spectrum is very broad: thus, they can be excited with radiation of different wavelengths. Nanocrystal quantum dots have the advantage of being very bright when they fluoresce: thus, they can be used in small quantities, in contrast to organic fluorophores, which have a weaker fluorescence intensity.

Thus, the luminescent characteristics of semiconductor nanocrystals mean that they can be used as tracers in a fluid as they can easily be detected.

The advantage of quantum dots also resides in the fact that it is possible to control their optical properties by modifying their size, their shape, their chemical compositions (for example by incorporating into them specific atomic elements which are generally known as dopants), and their surface properties. As an example, non-spherical quantum dots, i.e. which are cylindrical in shape or in the form of platelets, have the advantage over spherical quantum dots of emitting polarized light: this property may be a supplemental advantage for detection and identification using a measuring system in accordance with the invention (when this integrates polarizers, for example).

By means of the detector of the measuring system in accordance with the invention, it is possible to measure the wavelength emitted by a fluorescent radiation from semiconductor nanocrystals. Thus, it is possible to differentiate the semiconductor nanocrystals present in the fluid, which makes it possible to simultaneously measure the quantity of different types of semiconductor nanocrystals present in the fluid. Similarly, because of this property, it is possible to measure the quantity of the different additives present in the fluid to be analysed, by also knowing the semiconductor nanocrystals which have been used to specifically label the additives to be analysed and determined. Thus, it is possible to measure the concentrations of different additives or to measure the additives injected at various locations, or at different times.

There are different types of luminescent semiconductor nanocrystals, in particular those described in the following non-limiting list:
1. Fluorescent semiconductor nanocrystals (which emit a light signal when illuminated by electromagnetic radiation) can be distinguished:
    Semiconductor nanocrystals can exist in the form of fluorescent semiconductor nanocrystals which are pure and constituted by a single atomic element belonging to column IV of the periodic table (such as silicon or germanium).
    Type II-VI semiconductor nanocrystals (so named because of their electron structure) are interesting from the point of view of their optical properties, in particular fluorescence. These semiconductors (which associate one or more anions with one or more cations) include the following:
        zinc sulphide (ZnS), zinc oxide (ZnO), which emit in the ultraviolet, as well as cadmium sulphide (CdS).

zinc selenide (ZnSe), cadmium sulphide (CdS), cadmium selenide (CdSe), cadmium telluride (CdTe), lead sulphide (PbS), which emit over a spectrum ranging from the ultraviolet to the infrared, passing through the visible.

lead telluride (PbTe), lead selenide (PbSe), for the infrared.

The fluorescent semiconductor nanocrystals may also be in the form of a semiconductor core coated in a shell which is itself semiconducting. This shell can be used to protect the core (for example from oxidation, and/or from leaching caused by the fluids in which the semiconductor nanocrystals are caused to circulate or dwell) and to improve the quantum yields (i.e. the quality of the fluorescence). These single-shell semiconductor nanocrystals principally include:

a core of cadmium selenide (CdSe) coated in a shell of zinc (Zn) and sulphur (S): CdSe/ZnS other possible examples: CdSe/ZnSe, CdSe/CdS, InP/ZnS, etc.

The fluorescent semiconductor nanocrystals also exist in the form of a core coated with several shells: these are known as multi-shell quantum dots. These quantum dots have the advantages of being less fragile as regards the shell (and thus protecting the core better), and of having the highest quantum yields (of the order of 80% to 90%). Examples of quantum dots of this type are, for example:

CdSe/CdS/ZnS

CdSe/ZnSe/ZnS

The fluorescent semiconductor nanocrystals may also be composed of three atomic elements from columns I, III and VI of the periodic table. Examples of semiconductor nanocrystals of this type are:

$CuInSe_2$ $CuInS_2$

CdSeTe

CdHgTe $ZnS/Zn_{1-x}Cd_xS$, where x designates a number in the range zero to one.

2. Phosphorescent semiconductor particulate materials (which emit a light signal after having been illuminated by electromagnetic radiation) can be distinguished. These compounds can be divided into two categories:

Phosphorescent semiconductor nanocrystals, including:

zinc sulphide doped with manganese (ZnS:Mn)

zinc sulphide doped with europium (ZnS:Eu)

calcium sulphide doped with europium (CaS:Eu)

strontium sulphide doped with europium (SrS:Eu)

strontium sulphide doped with europium and dysprosium (SrS:Eu,Dy)

strontium sulphide doped with europium and copper (SrS:Eu,Cu)

Micrometric and sub-micrometric particles of phosphorescent semiconductors (these particles may be obtained, for example, by grinding phosphorescent materials), including:

$SrAl_2O_4$:Eu,Dy, $CaAl_2O_4$:Eu,Nd,B $Y_2O_2S$:Eu,Mg,Ti $SrSiO_4$:Eu $Ba_{13}Al_{22}Si_{10}O_6$:Eu $Sr_6Al_{18}Si_2O_{37}$:Eu $CaAl_2Si_2O_8$:Eu $SrAl_2Si_2O_8$:Eu $BaAl_2Si_2O_8$:Eu

In accordance with one embodiment of the invention, phosphorescent semiconductor nanocrystals may be used in order to detect them. In addition, luminescent nanocrystals may be used for detection and quantitative measurement thereof.

By means of the measuring system in accordance with the invention, it is possible to detect luminescent semiconductor nanocrystals mixed directly with fluid or luminescent semiconductor nanocrystals which label (by grafting, adsorption, by chemical bonding, etc) a compound (molecule, monomer, polymer, copolymer, surfactant, metallic oxide, mineral particle, etc) which might be found in the fluid. It may, for example, be a luminescent semiconductor nanocrystal labelling a polymer, a copolymer, a surfactant or molecules of various chemical natures. This labelling may be carried out either by (chemical) grafting to the molecules (for example in the case of polymers, copolymers, monocatenary, bicatenary surfactants, polymers or surfactants, or any organic molecule itself grafted to a clay or any other mineral), or by incorporation directly into the structure of the molecules (for example in the case of inorganic additives such as silica, proppants), barite, or other oxides such as titanium oxide), or by coating the molecules and the luminescent semiconductor nanocrystals (for example coating solid fillers and semiconductor nanocrystals with a layer of silica).

Figure 1:
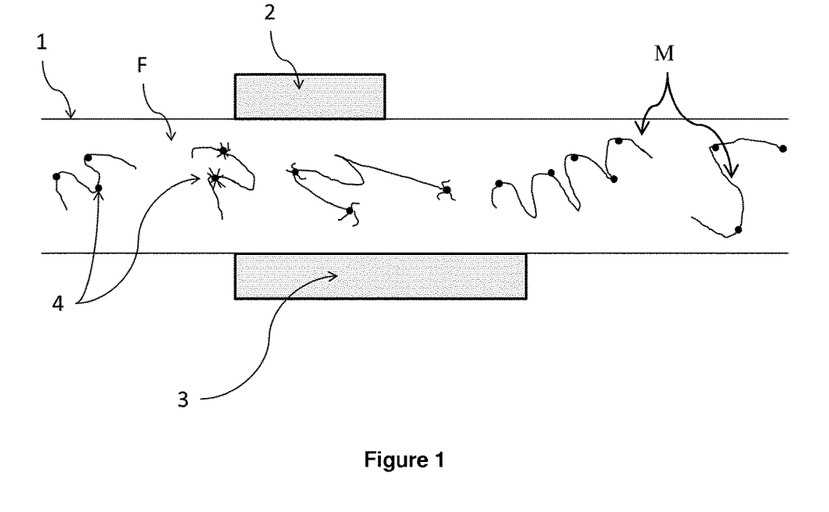
FIG. 1 illustrates a measuring system in accordance with the invention.

FIG. 1 illustrates a measuring system in accordance with one embodiment of the invention. A fluid F flows in a circulation device 1. The circulation device 1 shown is a tubular channel. The fluid comprises molecules M onto which luminescent semiconductor nanocrystals 4 have been grafted. The dimensions of the molecules M and the semiconductor nanocrystals 4 have been increased for better understanding of FIG. 1. In addition, their shapes are not representative. The molecules M may in particular be polymers of different types and different natures, hence their different shapes. Similarly, the luminescent semiconductor nanocrystals 4 may be of different types, hence their distinct representations. The measuring system illustrated comprises a light source 2 which emits light radiation in the direction of the fluid F. At the same level as the source of light 2, the measuring system comprises a detector 3 placed at about 90° with respect to the incident radiation emitted by the light source, and which receives light radiation from the luminescent semiconductor nanocrystals 4 present in the fluid F.

In accordance with a variation, not shown, the detector may be placed at 180° with respect to the incidence of the incident light.

Figure 3:
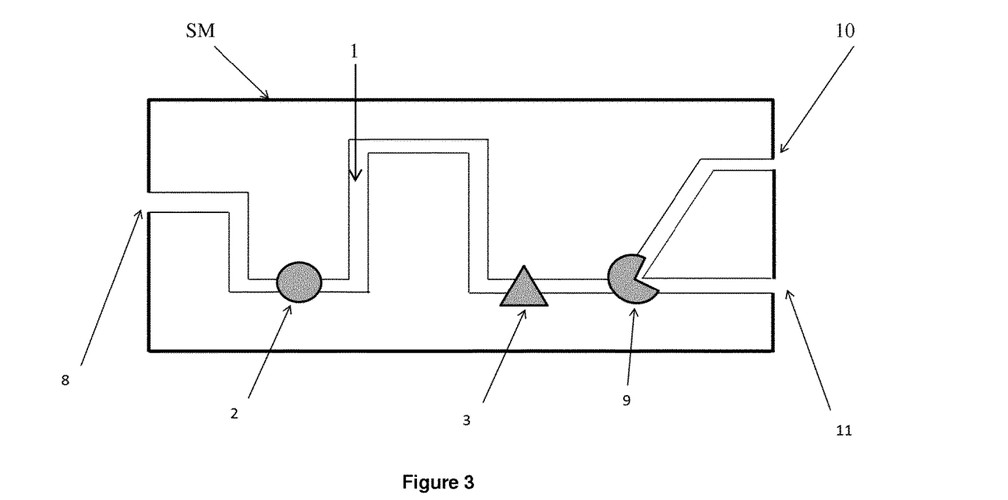
FIG. 3 represents a measuring system in accordance with one embodiment of the invention in which the measuring system is a microfluidic chip.
Figure 4:
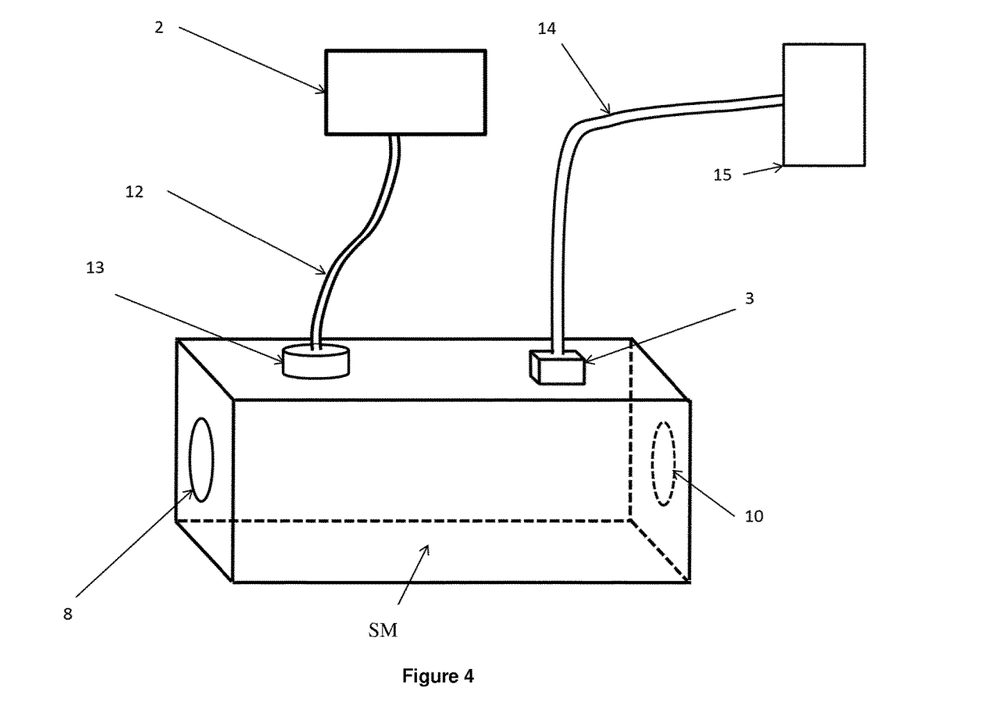
FIG. 4 is a three-dimensional view of a measuring system in accordance with one embodiment of the invention in which the measuring system is a microfluidic chip.

FIGS. 3 and 4 represent two variations of embodiments of the measuring system in accordance with the invention when the measuring system is a microfluidic chip. These two variations may be combined.

FIG. 3 is a top view of a measuring system SM in the form of a microfluidic chip comprising a micro-channel 1 for the circulation of liquid, a light source 2 placed close to the inlet 8 to the micro-channel, and a detection system 3 placed close to the outlet 10 or 11 from the micro-channel. The shape of the micro-channel 1 is illustrative; other shapes may be envisaged, in particular to limit the pressure drops.

In accordance with the embodiment of FIG. 3, which is not limiting in nature, the microfluidic chip may also comprise a shunting system 9 and at least two outlets 10 and 11. The shunting system allows the flow of fluid to be sorted as a function of the measurement by the detector 3. As an example, the outlet 10 may concern the fluid without semiconductor nanocrystals (or without additives), and the outlet 11 may concern the fluid containing semiconductor nanocrystals (or with additives). The shunting system 9 can thus be used to carry out supplemental analyses of the fluid.

FIG. 4 is a three-dimensional view of a measuring system of this type. The light source 2 may be a diode laser, or be formed by an optical fibre 12 connected to a diode laser 2. Furthermore, the light source may comprise an illumination device 13 for the micro-channel 1, which means that the light beam from the optical fibre can be enlarged. The detector 3 may be a photodetector, or a photodiode associated with a current amplifier. Furthermore, the detector 3 may be connected to a signal processing and analysis system 15 by means of a signal transfer system 14 which may in particular be formed by electrical wires.

In accordance with one embodiment of the invention, the measuring system may be installed directly in the principal conduit in which the fluid to be analysed is moving. In accordance with one exemplary embodiment, the measuring system can be in the form of a hollow tube, this tube being maintained and centred in the principal conduit by rods or bars resting on the internal walls of the principal conduit.

Figure 5:
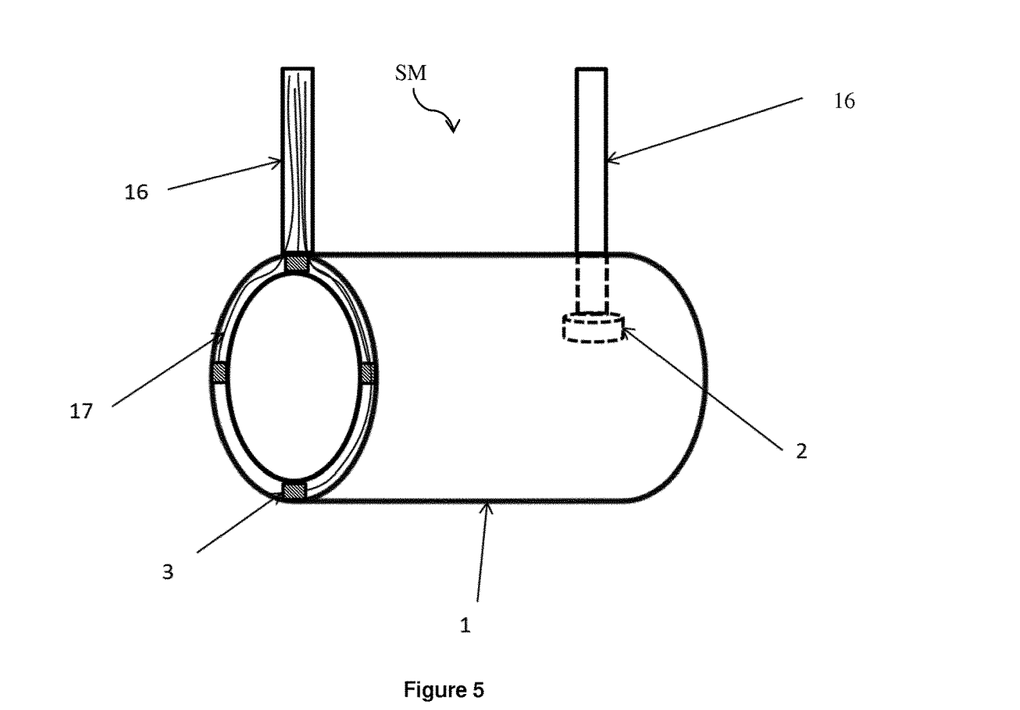
FIG. 5 illustrates a measuring system in accordance with one embodiment, the measuring system being intended for installation directly in the conduit in which the fluid to be analysed is circulating.
Figure 6:
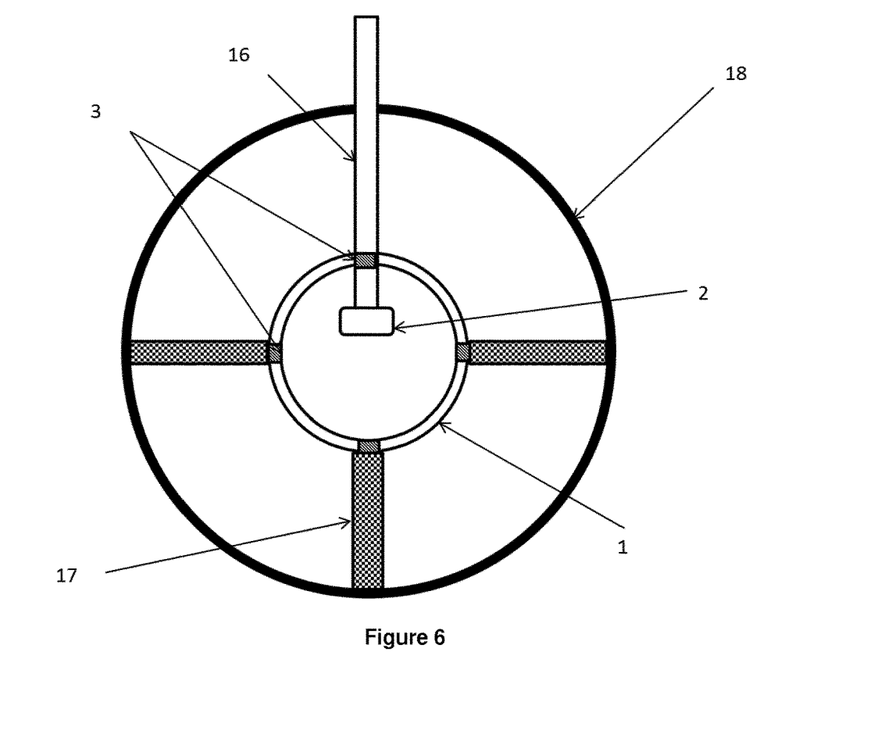
FIG. 6 illustrates a measuring system in accordance with the embodiment of FIG. 5 installed in a conduit.

FIGS. 5 and 6 respectively, in a non-limiting manner, represent an exemplary embodiment. FIG. 5 is a view of a measuring system SM alone, and FIG. 6 represents the measuring system SM placed in a conduit 18. In accordance with the embodiment illustrated, the measuring system SM has a substantially tubular shape 1. The measuring system SM comprises a light source close to one of its ends (upstream in the direction of circulation of fluid). Close to the other end (downstream in the direction of circulation of fluid) is at least one detector 3.

At least one anchoring rod 16 located upstream of the measuring system passes through the wall of the tube to maintain the light source 2 in place. This anchoring rod may be hollow so as to be able to actuate the light source 2. As an example, in the case in which the light source is a lamp operating using electricity, the wires pass inside the hollow anchoring rod 16. As an example, in the case in which the light source 2 is a diode laser or a diode laser assembly for illuminating the whole interior of the principal conduit 18, the hollow anchoring rod 16 allows electric wires or optical fibres to pass through.

At least one anchoring rod 16 located downstream of the measuring system is hollow so as to be able to install means for transporting signals from the detectors for fluorescence and/or phosphorescence 3. There is at least one fluorescence and/or phosphorescence detector 3. For a tube 1 with a small outlet diameter, a single fluorescence and/or phosphorescence detector 3 is sufficient to detect the signals emitted by the semiconductor nanocrystals. Depending on the outlet diameter of the tube 1 of the measuring system, several fluorescence and/or phosphorescence detectors 3 may be installed. In the case in which four fluorescence and/or phosphorescence detectors 3 are installed at the tube outlet, the angle between these four detectors may be 90°.

The anchoring system of the measuring system 1 in the principal conduit 18 is implemented by means of rods 16, 17 (the rods 16 act both as anchoring rods and as rods for transporting signals), which means that the measuring system 1 can be withdrawn easily. The minimum number of anchoring rods 16, 17 is two. In a preferred version of the invention, the number of anchoring rods 16, 17 is in the range six to eight. In the case in which the number of anchoring rods 16, 17 is equal to six, three rods 16, 17 may be positioned on the side of the fluid inlet (upstream side of the measuring system with respect to the direction of fluid circulation), and three other anchoring rods may be positioned on the side downstream of the measuring system. The angle between the three rods 16, 17 located on the same side of the measuring system may be fixed at 120°; this disposition ensures good stability of the measuring system in the duct. In the case in which the number of anchoring rods 16, 17 is equal to eight, four rods are positioned on the side of the fluid inlet (upstream side of the measuring system with respect to the direction of circulation of fluid), and four other anchoring rods are positioned on the downstream side of the measuring system. The angle between the four rods 16, 17 located on the same side of the measuring system is fixed at 90°; this disposition provides the measuring system with good stability in the duct.

In a version in which the quantity of semiconductor nanocrystals is to be measured, the source and fluorescence detector may be positioned at the same level (for example at the tube outlet); the fluorescence detector may be placed at 90° with respect to the source. The tube may comprise two shutters (one at the inlet, the other at the outlet) so as to be able to isolate the fluid in the tube and carry out measurements on a fluid at rest.

The present invention also concerns a facility for the treatment of an aqueous liquid. The treatment facility in accordance with the invention comprises:
  liquid treatment means, for example means for purifying the water in part from impurities and/or polluting products,
  means for selective distribution of liquid, comprising a plurality of outlets towards a plurality of circuits, these means allowing the flow of water into one of the circuits to be orientated in a programmed manner. The selective distribution means may be formed by a set of programmed valves,
  a conduit connecting the liquid treatment means and the selective liquid distribution means, the water circulating in the conduit from the treatment means towards the selective distribution means,
  a system for measuring the quantity of semiconductor nanocrystals present in the water, in accordance with any one of the variations described above. The measuring system may be disposed to bypass the conduit, i.e. the measuring system is in parallel to at least a portion of the conduit. A portion of the water circulates in the measuring system. Alternatively, the measuring system is installed directly in the conduit (in accordance with the embodiment of FIGS. 5 and 6); this type of installation can be used to analyse the fluid circulating in the conduit and not only a sample thereof.

In accordance with the invention, the selective distribution means are programmed to distribute water towards one of the circuits as a function of the measurement carried out by the measuring system. Thus, if the measuring system detects a certain quantity of semiconductor nanocrystals in the water (corresponding to a certain quantity of additive labelled by these semiconductor nanocrystals), the water is orientated in a first circuit, and if the measuring system detects few or no semiconductor nanocrystals in the water, the water is orientated into a second or $n^{th}$ circuit. In accordance with a variation of the invention, the selective distribution means comprise more than two outlets, the measuring system is capable of detecting several types of semiconductor nanocrystals (and thus, optionally, several additives), and the water is orientated into one of the circuits as a function of the type of additives detected due to the semiconductor nanocrystals present.

The various selectable circuits may comprise at least:
  a water storage circuit provided to store water, for example when the measurement indicates that the water contains semiconductor nanocrystals and thus that the quality of the water is not correct, the water is stored in order to be treated subsequently, a circuit for re-injecting water into a process using water, for example when the measurement indicates that the water does not contain or only contains a few semiconductor nanocrystals, and thus no additives, i.e. that the water is almost depolluted; thus, the water is either reused in the process or is discharged into the environment.

Figure 2:
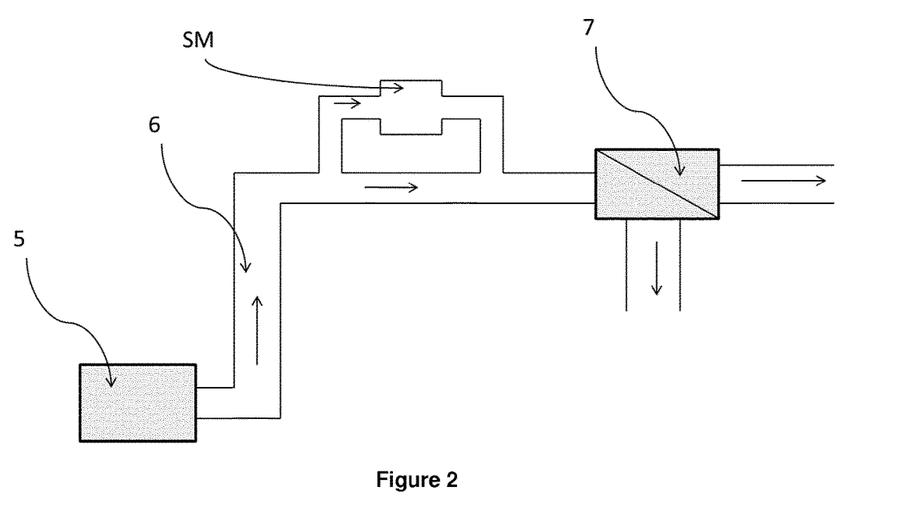
FIG. 2 illustrates a facility for the treatment of an aqueous liquid in accordance with one embodiment of the invention.

FIG. 2 illustrates an exemplary embodiment of a facility for the treatment of water in accordance with the invention. The installation comprises means 5 for the treatment of water, a conduit 6 and means 7 for the selective distribution of water. The conduit 6 connects the treatment means 5 to the collective distribution means 6, with the water circulating from the treatment means 5 to the selective distribution means 7. The selective distribution means 7 shown have two outlets, to orientate the water into two distinct circuits as a function of its command and control. The installation further comprises a measuring system SM as described above (with circulation devices, light source and detector). In this example, the measuring system SM is positioned as a bypass (in parallel) to the conduit 6. The measuring system SM detects the quantity of additives sought because of the fluorescence emitted by the semiconductor nanocrystals in the fluid and, as a function of this measurement, the selective distribution means are programmed and controlled to orientate the water towards one of the outlets, so that it is used correctly.

Applications

The measuring system in accordance with the invention may be used in any field in which the quantity of polluting additives present in a fluid, in particular water, has to be measured, these additives being identifiable due to the semiconductor nanocrystals grafted onto them. It is not necessary to label all of the additives with semiconductor nanocrystals: it is sufficient to use a certain quantity of grafted additives, these additives being used as labels for the quality of the water treatment. In the case of a treatment of water involving polymers, a quantity of 10% (more generally P %) of polymers grafted with fluorescent semiconductor nanocrystals may thus be used. If, after the treatment, the measuring system as described in the invention measures a concentration of polymers equal to $C_f$, the final real concentration, $C_{fr}$, of polymer will be equal to $C_f$ divided by 10% (more generally P %), assuming that the grafted and non-grafted polymers behave in the same manner in solution.

In accordance with one envisaged application, the measuring system may be used to measure the quantity of additive in the water produced by a process for developing or exploring a subterranean formation. In this application, an injection fluid comprising an additive is injected into a subterranean formation (for example for an enhanced oil recovery process, a process for developing source rock oils and gas, etc). This additive may take the form of organic molecules such as polymers, copolymers and/or surfactants, etc. It may also take the form of inorganic molecules such as clay minerals, or oxides (such as barite, silica, etc). The additive is labelled with at least one fluorescent semiconductor nanocrystal. The water produced by the development or exploration process circulates in the measuring system in accordance with the invention. Thus, determining the quantity of semiconductor nanocrystals present in the water means that the quantity of additives present in the water can be determined in-line and continuously, which means that suitable treatment or treatments for the water can be selected. By using several semiconductor nanocrystals to label the additives, it is possible to detect the presence of several additives in the water. In the case in which the treatment of the water employs different sequential steps, a measuring system may advantageously be placed at the end of each purification step so as to monitor the quality of the water throughout the overall treatment process. Thus, as soon as the water has the desired degree of purity, treatment of the water can then be stopped, making the process less expensive.

In accordance with another envisaged application, the measuring system may be used to detect the presence and/or to measure the quantity of pollutants in the water, for a water purification and/or depollution station. Thus, determining the quantity of luminescent semiconductor nanocrystals present in the water means that the quantity of pollutants in the water can be determined in-line and continuously in a manner such as to adapt the treatment of the water. By using several luminescent semiconductor nanocrystals to label the pollutants, it is possible to detect the presence of several pollutants.

Figure 7:
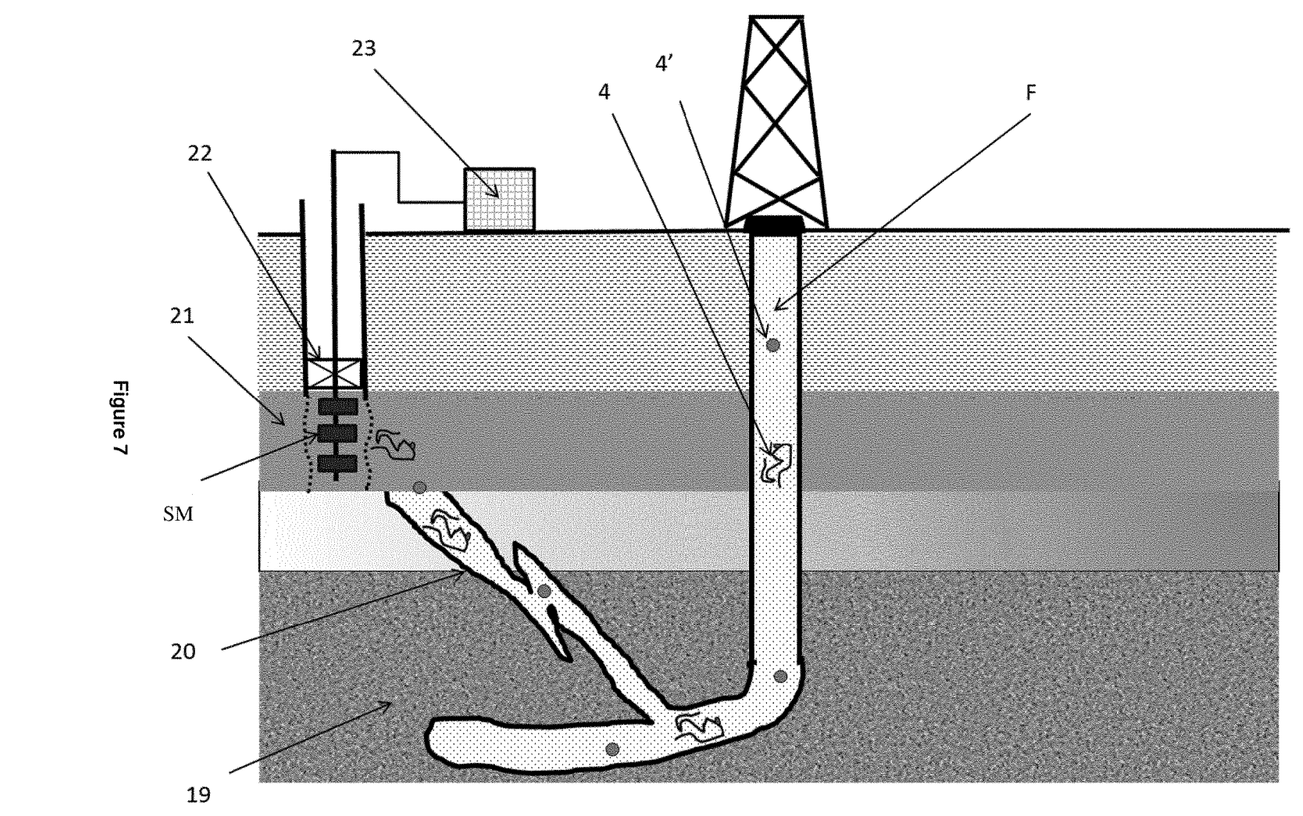
FIG. 7 illustrates a measuring system in accordance with the invention used as a sensor for monitoring and controlling the quality of aquifers.

In accordance with another envisaged application, the measuring system in accordance with the invention may be buried in a subterranean formation (such as, for example, an aquifer, ground water, etc) so as to be able to monitor the quality of the water, in particular in the case of developing source rock oils and gas (see FIG. 7). In fact, to develop these unconventional hydrocarbons, it is necessary to carry out hydraulic fracturing using fracturing fluids F which contain products which are potentially toxic and harmful to the biosphere. In the case in which one or more fracture(s) 20 generated by the hydraulic fracturing intercept(s) the aquifers 21 above the source rock 19, it is possible for a portion of the fluids F used for developing the source rock oils and gas 19 to rise along this or these fracture(s) 20 and pollute the aquifers 21 or ground water. The presence of one or more measuring systems SM buried in the aquifers 21 or ground water concerned thus means that pollution of these aquifers 21 or ground water can be detected. To this end, it is sufficient for the operators to incorporate a few ppm (parts per million) of luminescent semiconductor nanocrystals 4' into their fluids (fracturing fluids, for example) or to incorporate additives 4 labelled with at least one semiconductor nanocrystal. Using different luminescent semiconductor nanocrystals 4, 4' had the advantage of being able, for example, to identify the well responsible for the leak or, for example, to identify the operating company responsible for the leak. The principle of the measuring system SM remains the same as that described above: the fluid circulates inside a channel or a chamber by means of the natural flow of the aquifer 21. During its passage in the chamber, the fluid is illuminated by a light source. At the level of the light source, a detection system is placed (preferably at 90° with respect to the incident beam) and the fluorescence and/or phosphorescence signal is measured. In a preferred version of the invention, the semiconductor nanocrystals are excited with the aid of an optical fibre connected to a diode laser which is located on the surface. Interrogation of the measuring system may be periodic or continuous (for example throughout the duration of the fracturing operations, which are critical steps). Advantageously, interrogation of the measuring system may be digitally controlled with the aid of a measurement acquisition and interpretation system 23. The acquisition and interpretation system 23 may be installed at the surface. In addition, in order to prevent fluid from rising to the surface, a shutter block 22 may be placed above the measuring systems SM, so as to close the well via which they have been installed.

Furthermore, the invention concerns a method for detection and/or measurement of the quantity of at least one luminescent semiconductor nanocrystal (fluorescent or phosphorescent) present in a fluid. In this method, the following steps are carried out:
 a) the fluid is circulated in a circulation device;
 b) said circulation device is irradiated with light radiation, in particular by a light source; and
 c) the luminescence from said semiconductor nanocrystal is detected and/or measured in a zone of said fluid circulation device, said zone being exposed to said light radiation.

The luminescent semiconductor nanocrystals may be any of the luminescent semiconductor nanocrystals described above.

In addition, the detection and/or measurement method may be compatible with any of the variations of the detection and measuring system described above and may in particular comprise the following steps, alone or in combination:
 labelling the molecules present in the fluid with a luminescent semiconductor nanocrystal,
 circulating the fluid in the circulation device through a conduit bypass,
 preventing the circulation of fluid in the device during detection and/or measurement,
 after detection and/or measurement, shunting the fluid towards a plurality of circuits as a function of the detection and/or measurement.

The invention claimed is:

1. A system for the detection and/or measurement of the quantity of at least one luminescent semiconductor nanocrystal labeling an additive present in a fluid produced by a process for exploration or development of a subterranean formation, wherein the system for detection and/or measurement comprises a device for circulating the fluid, a light source oriented towards a portion of the device for circulating the fluid, and a detector which is capable of detecting and measuring the luminescence from the semiconductor nanocrystal circulating with the fluid, the detector being oriented towards a zone of the fluid circulation device downstream, with respect to a direction of circulation of the fluid, a longitudinal distance from the portion of the device for circulating the fluid exposed to light radiation from the light source, wherein the zone towards which the detector is oriented is downstream, with respect to the direction of circulation of the fluid, at a longitudinal distance (d) from the portion of the device for circulating the fluid exposed to light radiation from the light source, wherein the longitudinal distance (d) is at most equal to a rate of flow of fluid, v, multiplied by a maximum duration of luminescence, t, of the at least one luminescent semiconductor nanocrystal.

2. The system according to claim 1, in which the fluid is a complex solution or an aqueous liquid.

3. The system according to claim 1, in which the semiconductor nanocrystal labels a molecule which is potentially present in the fluid.

4. The system according to claim 1, in which the device for circulating the fluid is a channel bypassing a conduit in which the fluid circulates.

5. The system according to claim 1, in which the device for circulating the fluid is a microfluidic chip.

6. The system according to claim 1, in which the measuring system comprises at least one valve on each side of the circulation device.

7. The system according to claim 1, in which the light source emits monochromatic radiation.

8. The system according to claim 1, in which the light source emits polychromatic radiation.

9. The system according to claim 1, in which said light source emits polarized radiation.

10. The system according to claim 1, in which the detector is placed substantially at 90° or at 180° with respect to the incident beam emitted by the light source around the fluid circulation device.

11. The system according to claim 1, in which the detector comprises a photomultiplier and means for measuring the fluorescence and/or phosphorescence emission spectrum.

12. The system according to claim 1, in which the detector comprises a device for measuring the intensity of diffused light.

13. A facility for the treatment of an aqueous liquid, comprising means for treatment of the liquid, means for selective distribution of the liquid comprising at least two outlets, a transport conduit connecting the treatment means and the selective distribution means, and a system for detection and/or measurement according to claim 1, wherein the selective distribution means are programmed to distribute the liquid towards one of the outlets as a function of the measurement from the system for detection and/or measurement.

14. The installation according to claim 13, in which the detection and/or system for detection and/or measurement is disposed in a channel bypassing the transport conduit.

15. The installation according to claim 13, in which the detection and/or system for detection and/or measurement is disposed in the transport conduit.

16. A method for the detection and/or measurement of the quantity of at least one luminescent semiconductor nanocrystal labeling an additive present in a fluid produced by a process for exploration or development of a subterranean formation, wherein the following steps are carried out:
 a) the fluid produced by a process for exploration or development of a subterranean formation and containing the at least one luminescent semiconductor nanocrystal labeling an additive is circulated in a circulation device;
 b) the circulation device is irradiated with light radiation from a light source directed at a portion of the circulation device; and
 c) the luminescence of the semiconductor nanocrystal circulating with the fluid is detected and/or measured in a zone of the fluid circulation device, the zone being downstream, with respect to a direction of circulation of the fluid, a longitudinal distance from the portion of the device circulation device irradiated with the light radiation from the light source, wherein the zone towards which the detector is oriented is downstream, with respect to the direction of circulation of the fluid, at a longitudinal distance (d) from the portion of the circulation device exposed to light radiation from the light source, wherein the longitudinal distance (d) is at most equal to a rate of flow of fluid, v, multiplied by a maximum duration of luminescence, t, of the at least one luminescent semiconductor nanocrystal.

* * * * *